June 22, 1976
O. L. WEEKS
ROSE PLANT
Filed June 24, 1975
Plant Pat. 3,924
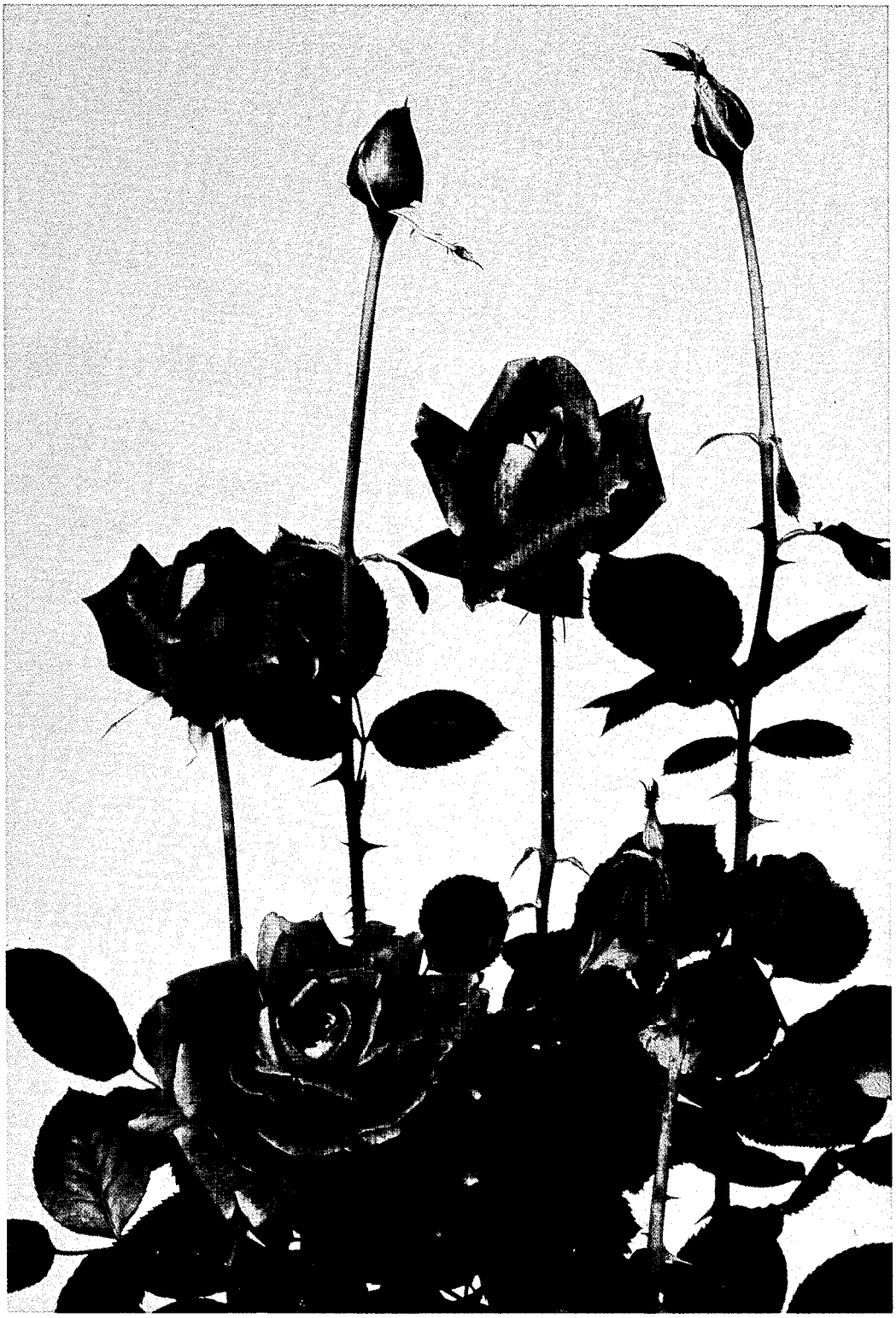

United States Patent

Plant Pat. 3,924

Patented June 22, 1976

1

3,924

ROSE PLANT

O. L. Weeks, 926 W. Philadelphia, Ontario, Calif. 91762

Filed June 24, 1975, Ser. No. 589,867

Int. Cl. A01h 5/00

U.S. Cl. Plt.—21 1 Claim

The present invention relates to a new and distinct variety of rose plant of the hybrid tea class, which was originated by me by crossing the rose variety known as "Forty-Niner" (Plant Pat. No. 792) with the rose variety known as "Oklahoma" (Plant Pat. No. 2,326), the former being the seed parent, and the latter being the pollen parent.

As the result of this breeding, I have produced a new and improved rose variety which is distinguished from its parents, as well as from all other rose varieties of which I am aware, as evidenced by the following unique combination of principal characteristics which are outstanding in the new variety:

(1) An attractive plant habit which is particularly attributable to its good height, density and compact canes which make it an ideal and useful garden rose plant;
(2) A distinctive blackish-red flower color, with the inside petals having a very velvety sheen and texture; and
(3) A distinctive and exceptionally heavy, sweet rose perfume flower fragrance which is quite often totally absent in many new rose varieties.

In comparison with its seed parent ("Forty-Niner") the new variety is a better grower and is more spreading, dense and compact than its more upright seed parent; the foliage of the new variey its heavy, waxy and dark green in color as disinguished from the lighter green color and duller finish of the foliage of the seed parent; the flower color of the new variety is a deep red (often referred to in the trade as "black-red"), with the inside petals having a very velvety sheen and texture, as distinguished from the bi-color red with straw yellow reverse petals that are typical of the flowers of the seed parent.

As compared with its pollen parent ("Oklahoma"), the plant habit of the new variey is more spreading, more symmetrical and more compact than that of the pollen parent; the flowers are smaller but have a much better bud form than those of this parent; the blackish velvety overlay of the dark red flower petals is much more pronounced in the new variety; and the flower fragrance is more distinctive and sweeter than the flower fragrance of the pollen parent.

Asexual reproduction of the new rose variety by budding, as performed by me at Ontario, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is possible to make the same in a color illustration of this character.

The following is a detailed description of my new variety, with color terminology in accordance with Munsell's Color Cascade, published by Munsell Color Company, Inc., of Baltimore, Md., except where general color terms of ordinary dictionary significance are obvious:

TYPE: Tall; bush; greenhouse and outdoor; seedling; for cut flowers and for garden decoration.
CLASS: Hybrid tea.
BREEDING: Seedling.
Seed parent—"Forty-Niner".
Pollen parent—"Oklahoma".

2

PROPAGATION: Holds its distinguishing characteristics through succeeding propagations by budding.

FLOWERS

LOCALITY WHERE GROWN AND OBSERVED: Ontario, Calif.
FLOWERS BORNE: Singly to stem; on strong, long stems.
QUANTITY OF BLOOM: From free to abundant, both outdoors and in greenhouse.
CONTINUITY: One season; from intermittent to continuous.
FRAGRANCE: Very strong.
Nature—Sweet rose perfume.
BUD:
Peduncle—From medium length to long; slender caliper; stiff; entirely smooth; no hairs or prickles.
Color—Light green.
Before calyx breaks—
Size—Medium.
Form—Short; pointed; with foliaceous appendages on the surface of the bud; with slender, bristle-like foliaceous parts extending beyond the tip of the bud equal to ¾ or more of its length.
As calyx breaks—Color—Medium Red, 40–9 at base, blending upward to Dark Red, 40–16.
As petals first open—
Size—Medium.
Form—Ovoid.
Color—Outside—Dark Red, 40–14, with small segment of greenish yellow at tip. Inside—Essentially Medium Red, 40–13, with some blending of Dark Red, 40–14.
Opening—Opens up well.
BLOOM:
Size (when fully open)—From 3 inches to 4½ inches.
Petalage—Very double; from 36 to 42 petals; arranged regularly.
Form—Cupped, full, high-centered and globular at first, but becoming high-centered and globular; petals being at first tightly rolled outward, but later becoming tightly cupped and rolled outward at maturity.
PETALS:
Texture—Thick; leathery; soft.
Appearance—
Inside—Velvety.
Outside—Satiny.
Shape—
Outside—Nearly round; scalloped; with apex flat; with 1 or 2 notches.
Intermediate—Round; scalloped; with apex flat; with 1 or 2 notches.
Inside—Round; irregularly scalloped; with apex flats; with 1 or 2 notches.

This description of a newly opened flower was made from a rose grown outdoors during the month of October at Ontario, Calif.

Color—
Outer petal—Outside surface—Medium Red, 40–11, with small basal segment of Greenish Yellow, 21–4.
Inside surface—Medium Red, 40–11, blending upward to Dark Red, 40–12 and then further blending to Black Red, 40–16.
Intermediate petal—Outside surface—Medium Red, 40–13, with a small basal segment of Greenish Yellow, 21–4. Inside surface—Blends from bottom upward from Medium Dark Red, 40–14 to Black Red, 40–16.

Inner petal—Outside surface—Medium Red, 40–13, with a small basal segment of Yellowish Green, 21–4. Inside surface—Bottom ⅓ of petal Medium Red, 40–13, blending upward to Black Red, 40–16.

This description was made from a rose that was open for three days outdoors during the month of October at Ontario, Calif.:

Color—
- Outer petal—Outside surface—Pink Red, 40–9, and with some streaking of Dark Red, 40–16, and with a small basal segment of Greenish Yellow, 21–4. Inside surface—Bottom ⅓ of petal Pinkish Lavender, 42–11, blending upward to Black Red, 40–16, with some modifying streaks of Medium Red, 41–12.
- Inner petal—Outside surface—Medium Red, 40–11, with a small basal segment of Greenish Yellow, 21–4. Inside surface—Bottom ⅓ of petal Medium Red, 40–13, blending upward to Black Red, 40–16.

General color effect—
- Newly opened flower—From medium red to a darker or almost black red.
- 3-days open—Darker red overall than the newly opened flower, with a general black red appearance.

Behavior—Drop off cleanly.

Flower longevity—
- On bush in garden—3 to 5 days in October.
- Cut roses grown outdoors and kept at living room temperature—5 days in October.

REPRODUCTIVE ORGANS

STAMENS: Very few; arranged irregularly about pistils; tucked in calyx.

FILAMENTS: Long; few with anthers.
- Color—Reddish.

ANTHERS: Medium size; open at various times.
- Color—Reddish white.

POLLEN: Sparse.
- Color—Lemon yellow.

PISTILS: Medium number.

STYLES: Uneven; short; thin; loosely separated.

STIGMA:
- Color—Whitish red.

OVARIES: All enclosed in calyx.

HIPS: None observed.

SEPALS: Permanent; long; straight; both curled and recurved.
- Color—From green to reddish.

PLANT

FOLIAGE:
- Leaves—Compound of 3, 5 and 7 leaflets; from normal number to abundant; medium size; fairly leathery and glossy.

Color—
- Mature — Upper surface — Moderately dark green. Under surface—Reddish green.
- Young—Upper surface—Moderately red. Under surface—Darker red.
- Rachis (the supporting stem of the compound leaf)—Medium weight. Upper side—Smooth. Under side—Moderately smooth, but minutely prickly.
- Stipules—Moderately long; medium width; with moderately long points turning out at an angle of less than 45°; recurved toward stem.

DISEASE AND INSECT RESISTANCE: Above average resistance to mildew, no evidence of blackspot, and average resistance to insects, as determined by comparison with other rose varieties grown under the same conditions at Ontario, Calif.

GROWTH:
- Habit—Tall; bushy; much-branched.
- Growth—Very free and vigorous.
- Main stems—
  - Color—Dull green.
  - Large prickles—Several; medium length; straight; with narrow base. Color—Light brown. Small prickles—None.
  - Hairs—None.
- Branches—
  - Color—Reddish green.
  - Large prickles—From several to many; long; straight; with long, narrow base. Color—Primarily green, with some reddishness.
  - Small prickles—Few. Color—Reddish.
  - Hairs—From none to few. Color—Reddish.
- New shoots—
  - Color—Dull reddish green.
  - Large prickles—Several; from medium length to long; straight; with short, narrow base. Color—Reddish at base, going to yellowish green.
  - Small prickles—None.
  - Hairs—Few. Color—Reddish.

I claim:

1. A new and distinct variety of rose plant of the hybrid tea class, substantially as herein shown and described, characterized particularly as to novelty by the unique combination of an attractive plant habit which is particularly attributable to its good height, density and compact canes which make it an ideal and useful garden rose plant; a distinctive blackish-red flower color, with the inside petals having a very velvety sheen and texture; and a distinctive and exceptionally heavy, sweet rose perfume flower fragrance which is quite often totally absent in many new rose varieties.

No references cited.

ROBERT E. BAGWILL, Primary Examiner